United States Patent
Benjamin et al.

(10) Patent No.: US 10,478,497 B2
(45) Date of Patent: Nov. 19, 2019

(54) COMBINATIONS OF INECALCITOL WITH AN ANTI-CD38 AGENT AND THEIR USES FOR TREATING CANCER

(71) Applicant: HYBRIGENICS SA., Paris (FR)

(72) Inventors: Susan Benjamin, Chatillon (FR); Cécile Planquette, Palaiseau (FR); Rémi Delansorne, Paris (FR)

(73) Assignee: HYBRIGENICS S.A., Paris (FR)

( * ) Notice: Subject to any disclaimer, the term of this patent is extended or adjusted under 35 U.S.C. 154(b) by 0 days.

(21) Appl. No.: 15/655,394

(22) Filed: Jul. 20, 2017

(65) Prior Publication Data

US 2018/0021432 A1     Jan. 25, 2018

Related U.S. Application Data

(60) Provisional application No. 62/364,561, filed on Jul. 20, 2016.

(51) Int. Cl.
| | | |
|---|---|---|
| *C07K 16/00* | (2006.01) | |
| *A61K 39/395* | (2006.01) | |
| *A61K 31/047* | (2006.01) | |
| *C07K 16/28* | (2006.01) | |
| *C07K 16/30* | (2006.01) | |
| *A61K 39/00* | (2006.01) | |

(52) U.S. Cl.
CPC ...... *A61K 39/39558* (2013.01); *A61K 31/047* (2013.01); *C07K 16/2896* (2013.01); *C07K 16/30* (2013.01); *C07K 16/3061* (2013.01); *A61K 2039/505* (2013.01)

(58) Field of Classification Search
None
See application file for complete search history.

(56) References Cited

U.S. PATENT DOCUMENTS

2009/0304710 A1* 12/2009 Park ................... A61K 47/6867
424/158.1

OTHER PUBLICATIONS

Desterke et al (Blood, Dec. 2015, 126:4020, ASH meeting abstract (Year: 2015).*

* cited by examiner

*Primary Examiner* — Lei Yao
(74) *Attorney, Agent, or Firm* — B. Aaron Schulman, Esq.; Stites & Harbison, PLLC (57) ABSTRACT

The present invention concerns combinations of inecalcitol with an anti-CD38 agent such as daratumumab, MOR 202 or isatuximab for the treatment of cancer, such as hematological malignancies by increasing or inducing the expression of CD-38 by inecalcitol.

1 Claim, 6 Drawing Sheets

COMBINATIONS OF INECALCITOL WITH AN ANTI-CD38 AGENT AND THEIR USES FOR TREATING CANCER

CROSS-REFERENCE TO RELATED APPLICATION

The present application claims the benefit to U.S. Provisional Patent Application Ser. No. 62/364,561, herein incorporated by reference.

FIELD OF THE INVENTION

The present invention relates to inecalcitol-based combination therapies in particular for treating cancer, such as hematological malignancies.

BACKGROUND OF THE INVENTION

Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Examples of malignancies derived from myeloid cells include acute myeloid leukemia, including acute promyelocytic leukemia, and chronic myeloproliferative diseases, including chronic myeloid leukemia.

Malignancies derived from T and NK cells including mature T cell and NK cell neoplasms include T-cell prolymphocytic leukemia, T-cell large granular lymphocytic leukemia, aggressive NK cell leukemia, adult T-cell leukemia/lymphoma, extranodal NK/T cell lymphoma, nasal type, enteropathy-type T-cell lymphoma, hepatosplenic T-cell lymphoma, subcutaneous panniculitis-like T-cell lymphoma, blastic NK cell lymphoma, Mycosis Fungoides/Sezary Syndrome, primary cutaneous CD30 positive T-cell lymphoproliferative disorders (primary cutaneous anaplastic large cell lymphoma C-ALCL, lymphomatoid papulosis, borderline lesions), angioimmunoblastic T-cell lymphoma, peripheral T-cell lymphoma unspecified, and anaplastic large cell lymphoma. B-cell malignancies include B-cell chronic lymphocytic leukemia, mantle cell lymphoma, Burkitt lymphoma, follicular lymphoma, diffuse large B-cell lymphoma, multiple myeloma, Hodgkin's lymphoma, hairy cell leukemia, primary effusion lymphoma and AIDS-related Non-Hodgkin's Lymphoma. Examples of B-cell non-Hodgkin's lymphomas are lymphomatoid granulomatosis, primary effusion lymphoma, intravascular large B-cell lymphoma, mediastinal large B-cell lymphoma, heavy chain diseases (including $\gamma$, $\mu$, and a disease), lymphomas induced by therapy with immunosuppressive agents, such as cyclosporine-induced lymphoma, and methotrexate-induced lymphoma. B-cell malignancies comprise more than 85% of diagnosed lymphomas.

Multiple myeloma (MM) is a B-cell malignancy characterized by the latent accumulation of secretory plasma cells in bone marrow with a low proliferative index and an extended life span. The disease ultimately attacks bones and bone marrow, resulting in multiple tumors and lesions throughout the skeletal system. Approximately 1% of all cancers, and slightly more than 10% of all hematologic malignancies, can be attributed to MM. Incidence of MM increases in the aging population, with the median age at time of diagnosis being about 61 years.

Currently available therapies for MM include chemotherapy, stem cell transplantation, Thalomid® (thalidomide), Revlimid® (lenalidomide), Velcade® (bortezomib), Aredia® (pamidronate), and Zometa® (zoledronic acid). Current treatment protocols, which include a combination of chemotherapeutic agents such as vincristine, BCNU, melphalan, cyclophosphamide, adriamycin, and prednisone or dexamethasone, yield a complete remission rate of only about 5%. Median survival is approximately 36-48 months from the time of diagnosis. Recent advances using high dose chemotherapy followed by autologous bone marrow or peripheral blood mononuclear cell transplantation have increased the complete remission rate and remission duration, yet overall survival has only been slightly prolonged, and no evidence for a cure has been obtained. Ultimately, all MM patients relapse, even under maintenance therapy with interferon-alpha (IFN-$\alpha$) alone or in combination with steroids.

One of the most promising novel agents is the human IgG1 anti-CD 38 monoclonal antibody daratumumab. Daratumumab induces killing of MM cells mainly via the activation of potent cytotoxic immune effector functions, including antibody-dependent cellular cytotoxicity (ADCC), antibody dependent cellular phagocytosis and complement-dependent cytotoxicity (CDC). Another mechanism of action is induction of apoptosis upon secondary cross-linking. Anti-myeloma activity has also been demonstrated in mouse xenograph models and more importantly in a humanized mouse model. Daratumumab has been recently authorized in the US and worldwide under the trade name Darzalex®, as a single agent for the treatment of patients with multiple myeloma who have received at least three prior lines of therapy including a proteasome inhibitor (PI) and a immuno modulatory agent or who are double refractory to PI and an immune modulatory agent. Treatment with daratumumab is clinically effective, but there is a marked heterogeneity of response with a fraction of MM patients that does not respond to daratumumab as a single agent. It is currently unknown which mechanisms underlie the differential therapeutic efficacy of daratumumab but the levels of expression of CD38 on the surface of MM cells are positively correlated with the rate of partial clinical response to daratumumab (Nijhof et al., Blood, 15 Jun. 2016; doi: 10.1182/blood-2016-03-703439 and Nijhof et al Leukemia, 2039-2049, 2015).

CD38 is a type II membrane protein. It is expressed on most naturally occuring MM malignant plasma cells, and is implicated in various hematological malignancies. CD38 can also be expressed in a variety of malignant hematological diseases of lymphoid lineage, including multiple myeloma, leukemias and lymphomas, such as B-cell chronic lymphocytic leukemia, T- and B-cell acute lymphocytic leukemia, Waldenstrom macroglobulinemia, primary systemic amyloidosis, mantle-cell lymphoma, pro-lymphocytic/myelocytic leukemia, follicular lymphoma, Burkitt's lymphoma, large granular lymphocytic (LGL) leukemia, NK-cell leukemia and plasma-cell leukemia. By contrast, CD38 has been less often reported as implicated in hematological malignancies of myeloid lineage, such as acute or chronic myeloid leukemias. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Other diseases, where CD38 expression could be involved, include, e.g., broncho-epithelial carcinomas of the lung, breast cancer (evolving from malignant proliferation of epithelial lining in ducts and lobules of the breast), pancreatic tumors, evolving from the β-cells (insulinomas), tumors evolving from epithelium in the gut (e.g. adenocarcinoma and squamous cell carcinoma), carcinoma in the prostate gland, and seminomas in testis and ovarian cancers. In the central nervous system, neuroblastomas express CD38.

Nevertheless, CD38 is generally not expressed in all patients suffering from some myeloid hematological diseases. It is expected that such CD38-negative cases would a priori not be responsive to anti-CD38 agents.

Thus, there is a need for additional therapies for the treatment of hematological diseases, including those expressing CD38 and those that do not express CD38.

SUMMARY OF THE INVENTION

Inecalcitol (14epi-, 19nor-, 23yne-, 1,25dihydroxy-cholecalciferol) is a vitamin D receptor agonist already characterized by a high anti-proliferative effect and a low calcemic potential, allowing its administration at high oral doses to human cancer patients. It has been designated as an orphan drug both by the American Food and Drug Administration and the European Commission for the treatment of chronic lymphoid leukemia (CLL) and of acute myeloid leukemia (AML) due to its high anti-proliferative activity on cancer cells in general and on malignant blood cells in particular.

It has now been surprisingly found and that is one object of the present invention that inecalcitol stimulates the expression of CD38 in that it increases the expression of CD38 in hematological malignancies that at least partially express CD38 (CD38-positive malignancies) and induces the expression of CD38 in hematological malignancies that do not express CD38 (CD38-negative malignancies).

It has been further shown that such stimulation is inecalcitol dose-dependent.

Such stimulation leads to the increase in the pre-existing expression of CD38 in CD38-positive hematological malignancies and leads to the appearance of CD38 on initially CD38-negative hematological malignancies.

Due to the stimulation of CD38 expression, both CD38-positive malignancies and CD38-negative malignancies are to be more responsive to anti-CD38 agents.

The combination of inecalcitol with an anti-CD38 agent thus involves a synergy on both types of malignancies.

According to a first object, the present invention provides for the combination of inecalcitol with an anti-CD 38 agent.

According to one embodiment, the combinations of the invention are suitable for simultaneous, separate, sequential or spread-over-time administration of each active ingredient, in any order.

According to another object, the present invention also concerns a pharmaceutical product comprising the combination of the invention wherein inecalcitol and the anti-CD38 agent are formulated in a juxtaposed but separate form.

According to a further object, the invention thus provides for the combination of an anti-CD38 agent with inecalcitol for use for the treatment of cancer.

According to a still further object, the invention thus provides for inecalcitol for use for increasing the clinical response to an anti-CD38 agent in a patient suffering from cancer.

According to another object, the present invention also provides for a method of treating patients suffering from cancer, comprising administering to said patients a therapeutically effective amount of inecalcitol in combination with a therapeutically effective amount of an anti-CD38 agent.

According to a further object, the present invention also provides for a method of increasing the clinical response to an anti-CD38 agent comprising administering to patients suffering from cancer a therapeutically effective amount of inecalcitol.

According to a still further object, the present invention provides for the use of inecalcitol in combination with an anti-CD38 agent for the preparation of a medicament for the treatment of cancer.

According to a still further object, the present invention provides for the use of inecalcitol for the preparation of a medicament for increasing clinical response to an anti-CD38 agent in a patient suffering from cancer.

For each of the objects, the following embodiments are contemplated:

Inecalcitol and the anti-CD38 agent may be formulated in separate pharmaceutical compositions, according to their respective route of administration.

According to an embodiment, inecalcitol may be administered via the oral or parenteral routes. Suitable total dose may be comprised between 1.5 and 20 mg per day, preferably by the oral route According to an embodiment, the anti-CD38 agent may be generally administered via the parenteral (injectable) intravenous, intramuscular or subcutaneous routes. Suitable doses may be comprised between 50 mg and 2000 mg, repeated at a frequency between once a week and once a month.

The pharmaceutical products according to the invention may be suitable for the oral, sublingual, sub-cutaneous, intramuscular, intra-venous, topical, local, intranasal or transdermal administration.

In said pharmaceutical products, the active agents may generally be administered as a unitary dosage form. The appropriate unitary dosage forms comprise the oral forms, such as tablets, hard or soft gelatin capsules, powders, granules and oral solutions or suspensions, the sublingual, buccal, intranasal forms, by inhalation, the topical, transdermal, sub-cutaneous, intramuscular or intra-venous forms.

According to an embodiment, said cancer is a hematological malignancy, including CD38-positive hematological malignancy and CD38-negative hematological malignancy.

CD38-positive hematological malignancies include promyelocytic leukemia, histiocytic lymphoma, multiple myeloma (MM), B- or T-acute lymphoblastic leukemia (B-ALL, T-ALL), classical Hodgkin lymphoma (cHL), non-Hodgkin lymphoma (NHL), diffuse large B-cell lymphoma (DLBCL), Burkitt's lymphoma (BL), follicular lymphoma (FL) or mantle-cell lymphoma (MCL); more particularly, the CD38-positive disorder is multiple myeloma.

CD38-negative hematological malignancies include in particular acute myeloid leukemia.

Inecalcitol transforms such disorders into a CD38-positive malignancy therefore amenable to further treatment with an anti-CD38 agent.

According to an embodiment, inecalcitol is therefore administered prior to the treatment with the anti-CD38 agent.

The combination of an anti-CD38 agent with inecalcitol for use for the treatment of cancer according to the invention is therefore suitable for conducting a prior administration with inecalcitol until the hematological malignancy expresses a sufficient level of CD38, followed by subsequent administration of the anti-CD38 agent.

Alternatively, the combination of an anti-CD38 agent with inecalcitol for use for the treatment of cancer according to the invention is therefore suitable for conducting a sequential administration with inecalcitol and the anti-CD38 agent so as to maintain a continuous sufficient level of CD38, targeted by the anti-CD38 agent.

The sufficient level of expression of CD38 is generally determined by the practitioner, depending on the type of disease, the condition of the patient and the stage of the disease or the effects of prior treatments.

The combination of an anti-CD38 agent with inecalcitol for use for the treatment of cancer according to the invention is also suitable for the treatment of patients being resistant (CD38-negative) or having acquired resistance (having lost CD38 expression) to treatment with the anti-CD38 agent.

According to an embodiment, the anti-CD38 agent is an anti-CD38 antibody, or a single chain or fragment thereof capable of binding to CD38.

According to an embodiment, said anti-CD38 agent is daratumumab, isatuximab, MOR202, or another anti-CD38 antibody or a single chain or fragment thereof capable of binding to CD38. More particularly, the anti-CD38 agent is daratumumab.

Daratumumab is described in U.S. Pat. No. 7,829,693. Other exemplary anti-CD38 antibodies that may be used in the methods of the invention include those described in Intl. Pat. Publ. No. WO05/103083, Intl. Pat. Publ. No. WO06/125640, Intl. Pat. Publ. No. WO07/042309, Intl. Pat. Publ. No. WO08/047242 or Intl. Pat. Publ. No. WO14/178820. Anti-CD38 antibodies used in the methods of the invention disclosed herein, including in the numbered embodiments listed below, may also be selected de novo from a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated from for example phage display libraries expressing antibody heavy and light chain variable regions as fusion proteins with bacteriophage pIX coat protein as described in Shi et al., J. Mol. Biol. 397:385-96, 2010 and PCT Intl. Publ. No. WO09/085462). The antibody libraries may be screened for binding to human CD38 extracellular domain, obtained positive clones further characterized, Fabs isolated from the clone lysates, and subsequently cloned as full length antibodies. Such phage display methods for isolating human antibodies are established in the art. See for example: U.S. Pat. Nos. 5,223,409; 5,403,484; and 5,571, 698, U.S. Pat. Nos. 5,427,908, 5,580,717, 5,969,108, 6,172, 197, 5,885,793; 6,521,404; 6,544,731; 6,555,313; 6,582, 915; and 6,593,081.

The variable regions of the anti-CD38 antibodies may be obtained from existing anti-CD38 antibodies, and cloned as full length antibodies or into various antibody formats and fragments using standard methods. Exemplary variable regions binding CD38 that may be used are described in Intl. Pat. Publ. Nos. WO05/103083, WO06/125640, WO07/042309, WO08/047242, WO12/092612, WO06/099875 and WO11/154453A1.

As used herein:

"CD38" refers to the human CD38 protein (synonyms: ADP-ribosyl cyclase 1, cADPr hydrolase 1, Cyclic ADP-ribose hydrolase 1). Human CD38 has the amino acid sequence shown in SEQ ID NO: 1.

"Synergy", "synergism" or "synergistic" mean more than the expected additive effect of a combination of active agents.

"In combination with" as used herein means that two or more active agents may be administered to a subject together in a mixture, concurrently as single agents, or sequentially as single agents in any order.

The terms "treat" or "treatment" refer to therapeutic treatment wherein the object is to slow down (lessen) an undesired physiological change or disease, or provide a beneficial or desired clinical outcome during treatment, such as the development, growth or spread of tumor or tumor cells. Beneficial or desired clinical outcomes include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those subjects already with the undesired physiological change or diseases well as those subjects prone to have the physiological change or disease.

A "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic result include, for example, stimulation of biomarkers such as CD38 expression, improved well-being of the patient, reduction of a tumor burden, arrested or slowed growth of a tumor, and/or absence of metastasis of cancer cells to other locations in the body.

"CD38-positive hematological malignancy" refers to a hematological malignancy characterized by the presence of tumor cells expressing CD38 including leukemias, lymphomas and myeloma. Examples of such CD38-positive hematological malignancies are precursor B-cell lymphoblastic leukemia/lymphoma and B-cell non-Hodgkin's lymphoma, acute promyelocytic leukemia, acute lymphoblastic leukemia and mature B-cell neoplasms, such as B-cell chronic lymphocytic leukemia(CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma (MM), plasma cell leukemia, post-transplant lymphoproliferative disorder, Waldenstrom's macroglobulinemia, plasma cell leukemias, T- and B-cell acute lymphocytic leukemia, primary systemic amyloidosis, lymphoma, promyelocytic leukemia, Burkitt's lymphoma, large granular lymphocytic (LGL) leukemia, NK-cell leukemia, plasma-cell leukemia and anaplastic large-cell lymphoma (ALCL).

CD38-positive hematological malignancies include more particularly multiple myeloma, B- or T-acute lymphoblastic leukemia (B-ALL, T-ALL), classical Hodgkin lymphoma (cHL), non-Hodgkin's lymphoma, diffuse large B-cell lymphoma (DLBCL), Burkitt's lymphoma (BL), follicular lymphoma (FL) or mantle-cell lymphoma (MCL).

"CD38-negative hematological malignancy" refers to a hematological malignancy characterized by the absence of tumor cells expressing CD38. CD38-negative hematological malignancies include more particularly acute myeloid leukemia.

"Antibodies" as used herein is meant an immunological agent in a broad sense and includes immunoglobulin molecules including, monoclonal antibodies including murine, human, human-adapted, humanized and chimeric monoclonal antibodies, antibody fragments, bispecific or multispecific antibodies, dimeric, tetrameric or multismeric antibodies, and single chain antibodies.

"Antibody fragments" as used herein refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CHI domains, a F(ab)2 fragment, a bivalent fragment comprising two Fab fragments linked by a disulfide bridge at the hinge region, a Fd fragment consisting of the VH and CHI domains; a Fv fragment consisting of the VL and VH domains of a single arm of an antibody, a domain antibody (dAb) (Ward et al., Nature 341:544-546, 1989), which consists of a VH domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Intl. Pat. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

"Isolated antibody" as used herein refers to an antibody or antibody fragment that is substantially free of other antibodies having different antigenic specificities (e.g., an antibody that specifically binds CD38). An isolated antibody that specifically binds CD38, however, may have cross-reactivity to other antigens, such as orthologs of human CD38 such as *Macaca fascicularis* (cynomolgus) CD38. Moreover, an isolated antibody may be substantially free of other cellular material and/or chemicals. An antibody variable region consists of a "framework" region interrupted by three "antigen binding sites". The antigen binding sites are defined using various terms: Complementarity Determining Regions (CDRs), three in the VH (HCDR1, HCDR2, HCDR3), and three in the VL (LCDR1, LCDR2, LCDR3) are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991); "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites.

"Humanized antibody" refers to an antibody in which the antigen binding sites are derived from non-human species and the variable region frameworks are derived from human immunoglobulin sequences. Humanized antibodies may include substitutions in the framework so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin where the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. A human antibody may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a human antibody may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of human antibody.

Isolated humanized antibodies may be synthetic. Human antibodies may be generated using systems such as phage display incorporating synthetic CDRs and/or synthetic frameworks, or can be subjected to in vitro mutagenesis to improve antibody properties.

"Recombinant antibody" as used herein includes all antibodies that are prepared, expressed, created or isolated by recombinant means, such as antibodies isolated from an animal (e.g., a mouse or a rat) that is transgenic or transchromosomal for human immunoglobulin genes or a hybridoma prepared therefrom (described further below), antibodies isolated from a host cell transformed to express the antibody, antibodies isolated from a recombinant combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

"Monoclonal antibody" as used herein refers to a preparation of antibody molecules of single molecular composition. A monoclonal antibody composition displays a single binding specificity via its VH, VL and/or VH/VL pair and affinity for a particular epitope, or in a case of a bispecific monoclonal antibody, a dual binding specificity to two distinct epitopes.

"Epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope may be composed of contiguous and/or noncontiguous amino acids that form a conformational spatial unit. For a noncontiguous epitope, amino acids from differing portions of the linear sequence of the antigen come in close proximity in 3-dimensional space through the folding of the protein molecule.

"Variant" as used herein refers to a polypeptide or a polynucleotide that differs from a reference polypeptide or a reference polynucleotide by one or more modifications for example, substitution, insertion or deletion.

DETAILED DESCRIPTION AND EXEMPLARY EMBODIMENTS

Examples

Cell Lines

HL-60 acute promyelocytic leukemia cell line was purchased from ECACC (cat. 98070106), U-937 hystiocytic lymphoma cell line and MM.1S multiple myeloma cell line were purchased from ATCC (cat. CRL-2974 and cat CRL-1593,2, respectively), L-363 multiple myeloma cell line, L-428 classical Hodgkin lymphoma cell line and RS4,11 B-acute lymphoblastic leukemia cell lines were purchased from DSMZ (plasma cell leukemia, cat. ACC 49, cat. ACC 197 and cat. ACC 508, respectively). All cells were maintained in RPMI Medium 1640—GlutaMAX™ (Gibco 61870) except the RS4,11 cells in alpha-MEM Medium (Gibco 12571-063), supplemented with 10% heat inactivated charcoal stripped fetal bovine serum. All culture media were supplemented with 100 units/ml penicillin and 0.1 mg/ml streptomycin, and cell lines were cultured at 37° C. in a humidified atmosphere containing 5% CO2.

Flow Cytometry

Cells were treated for 72 h with various concentrations of inecalcitol (Hybrigenics, Paris, France) before labelling with fluorescent anti-human CD38 FITC (eBioscience, Vienna, Austria, cat. 11-0389-41) or the matched isotype control: mouse IgG1 K FITC (eBioscience, Vienna Austria, cat. 11-4714-41) for 1 h at 4° C. in native buffer (PBS, 2% BSA, 0.1% sodium azide). After cell wash, fluorescence was measured on an ACEA NovoCyte Flow Cytometer.

Results

Figure 1:
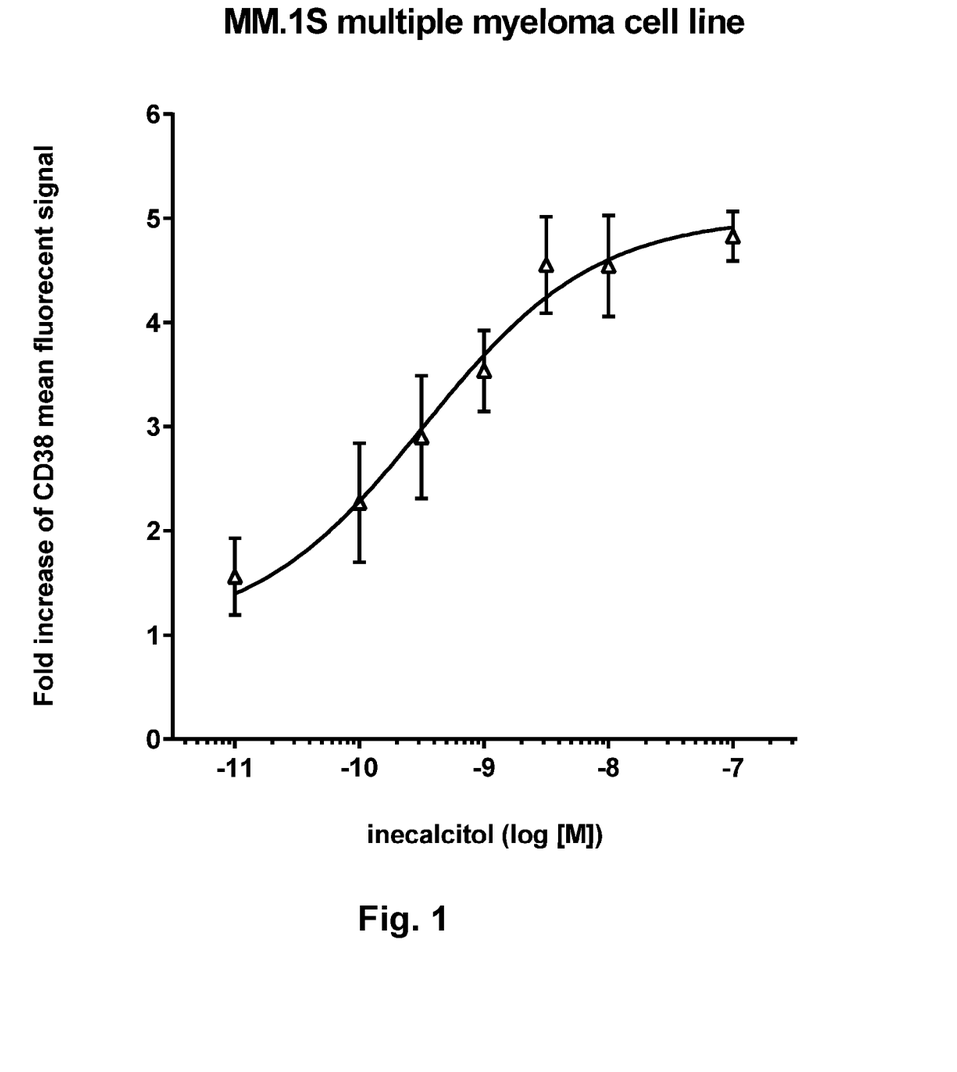
FIG. 1 shows that inecalcitol enhances CD38 expression on multiple myeloma (MM) MM.1S cell line in a dose dependent manner. The Y axis shows the fold increase of CD38 mean fluorescent signal.
Figure 2:
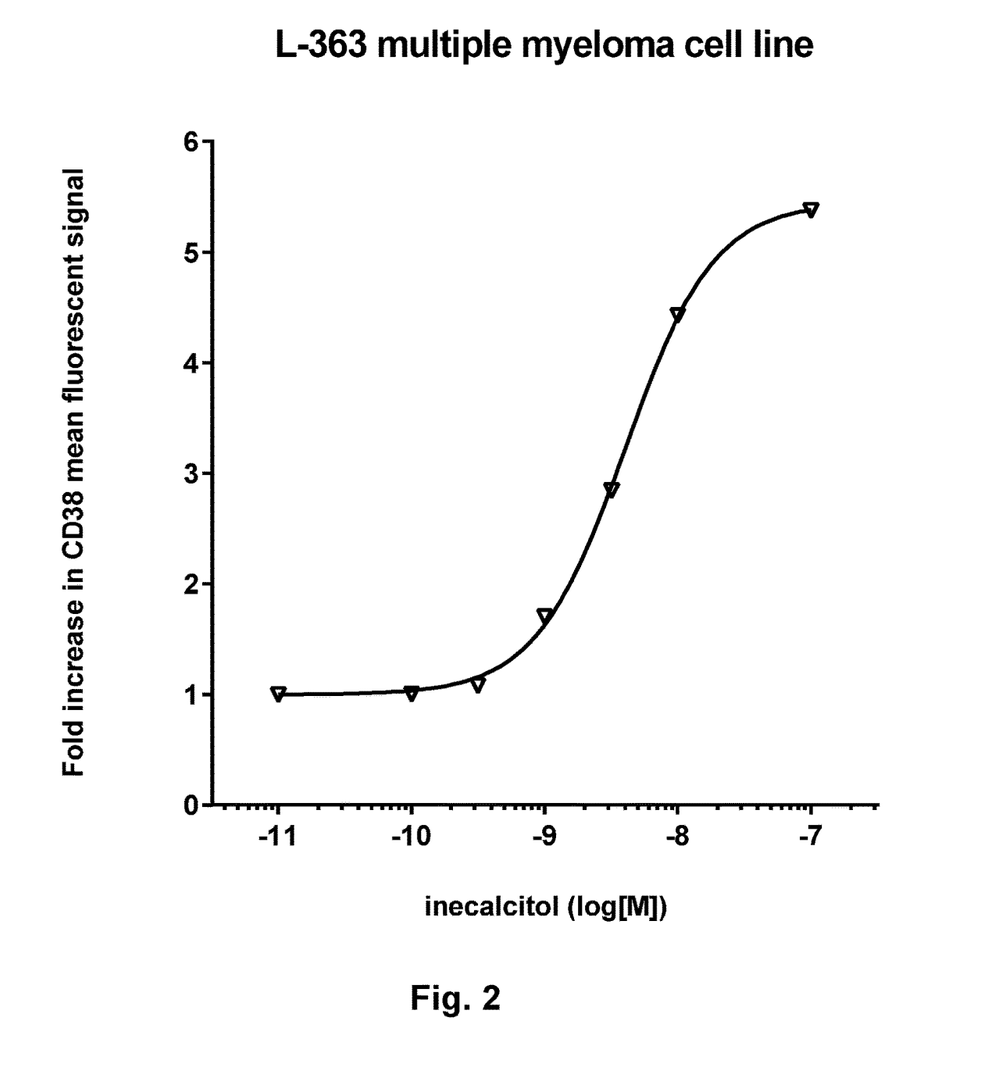
FIG. 2 shows that inecalcitol enhances CD38 expression on multiple myeloma (MM) L-363 cell line in a dose dependent manner. The Y axis shows the fold increase of CD38 mean fluorescent signal.
Figure 3:
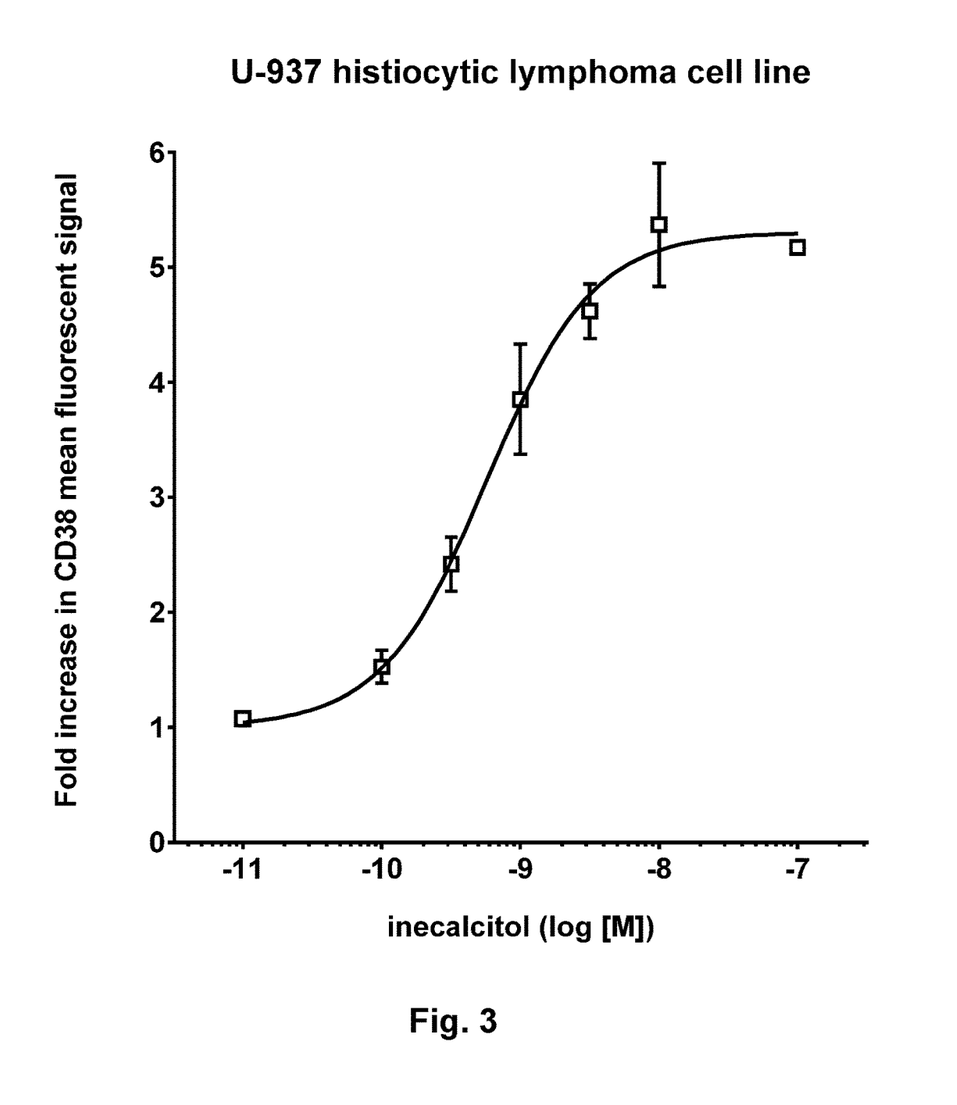
FIG. 3 shows that inecalcitol enhances CD38 expression on hystiocytic lymphoma cell line U-937 cell line in a dose dependent manner. The Y axis shows the fold increase of CD38 mean fluorescent signal.
Figure 4:
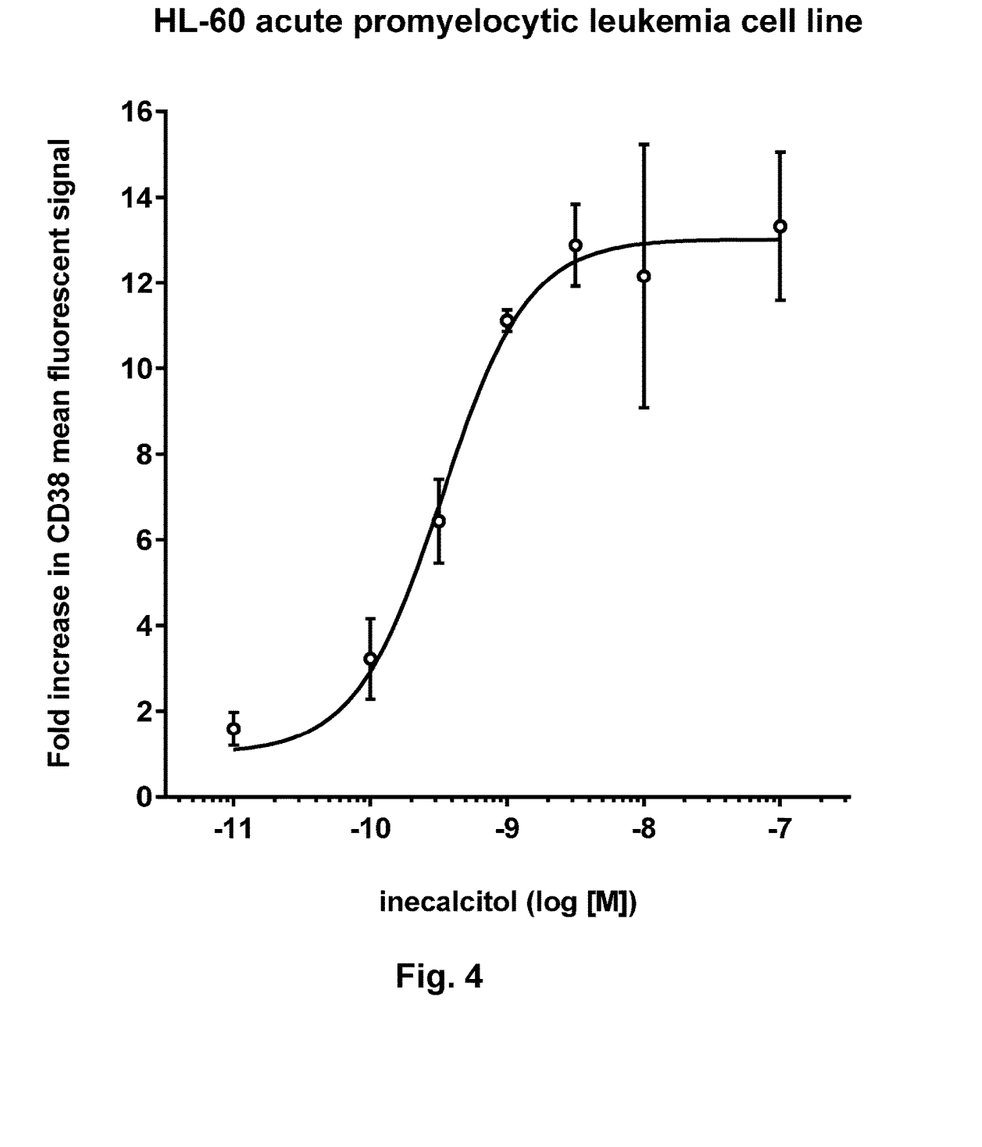
FIG. 4 shows that inecalcitol enhances CD38 expression on promyelocytic leukemia HL-60 cell line in a dose dependent manner. The Y axis shows the fold increase of CD38 mean fluorescent signal.
Figure 5:
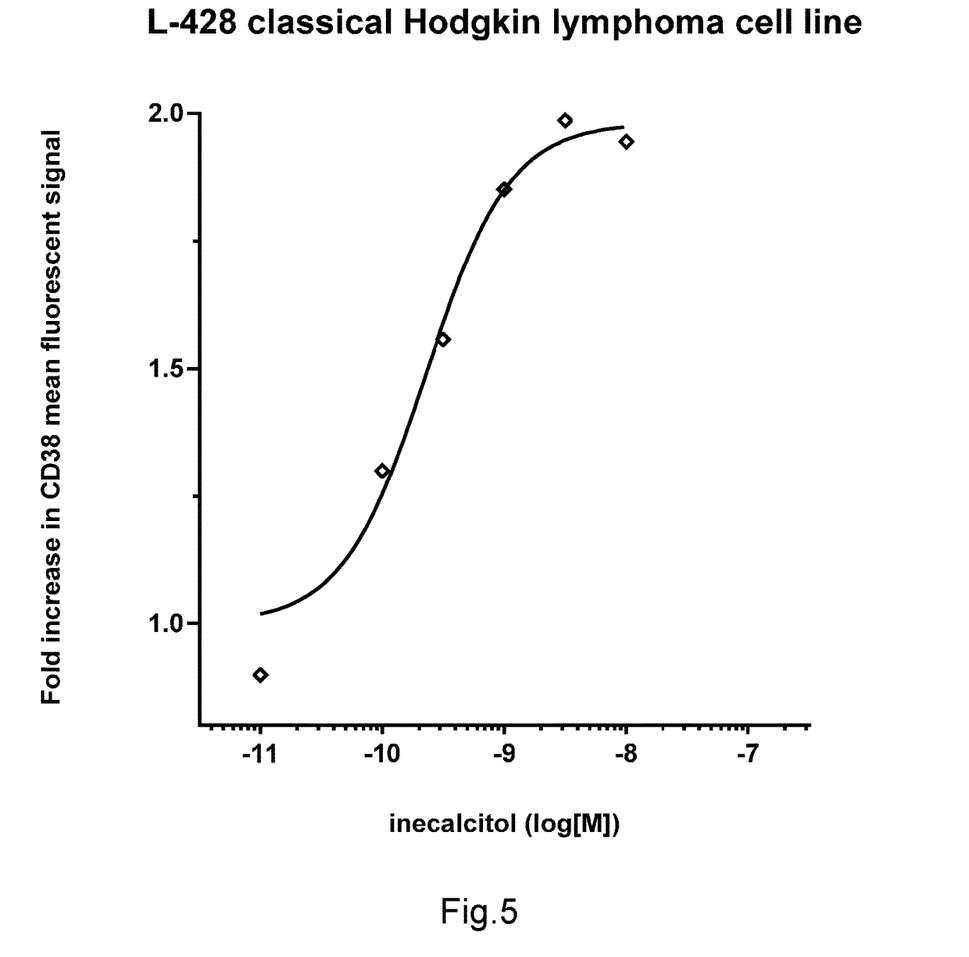
FIG. 5 shows that inecalcitol enhances CD38 expression on classical Hodgkin lymphoma cell line in a dose dependent manner. The Y axis shows the fold increase of CD38 mean fluorescent signal.
Figure 6:
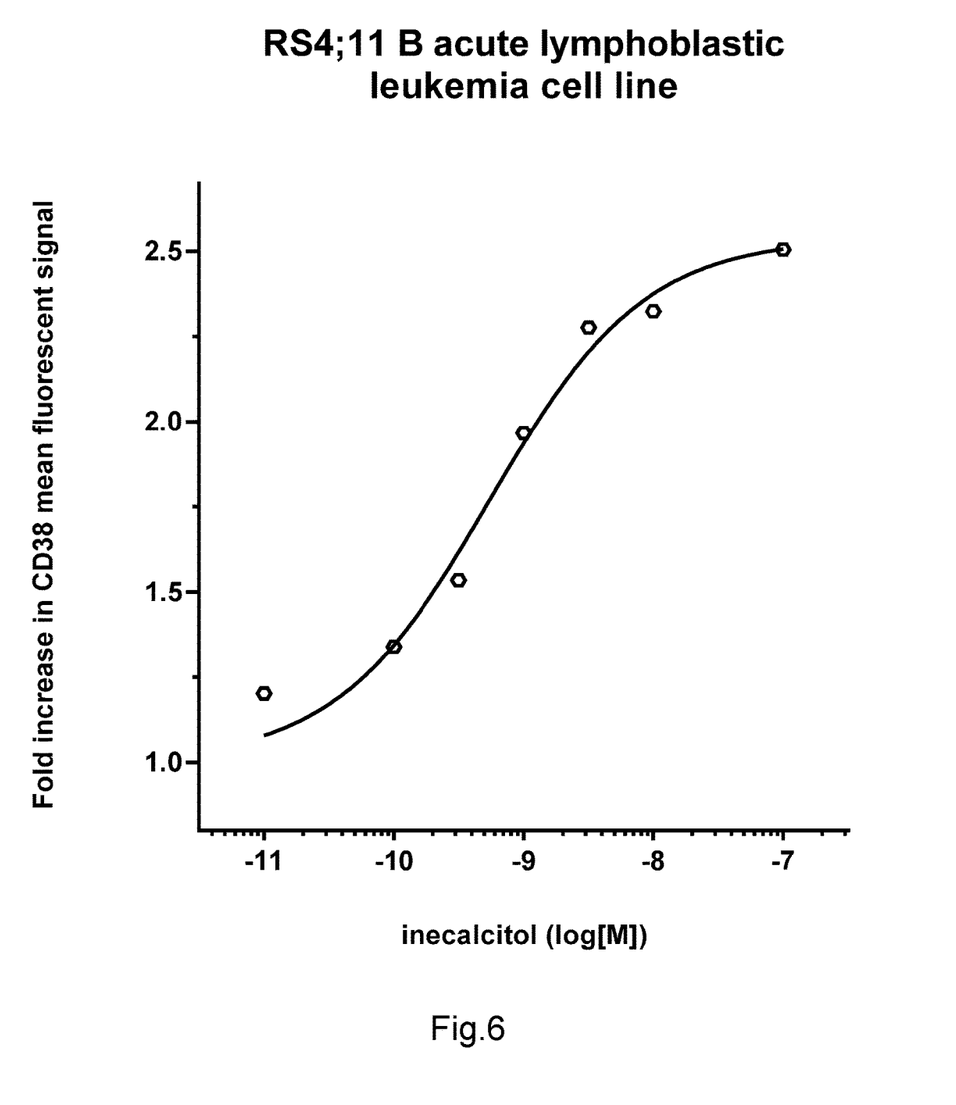
FIG. 6 shows that inecalcitol enhances CD38 expression on RS4.11 B-acute lymphoblastic leukemia cell line in a dose dependent manner. The Y axis shows the fold increase of CD38 mean fluorescent signal.

On each cell line, inecalcitol exerted a concentration-dependent stimulation of CD38 expression at the cell surface of the cells, as detected by binding of a CD38-specific, fluorescence-labelled antibody. The concentration of inecalcitol which triggered 50% of the maximum CD38 induction ($EC_{50}$) was 0.43 nM on HL-60 cells, 0.49 nM on MM.1s cells 0.57 nM on U-937 cells, 0.23 nM on L-428 cells and 0.55 nM on RS4,11 cells. L-363 cells were between 7 and 17 times less sensitive than the other cell lines, with an $EC_{50}$ of 4.0 nM.

Results are illustrated on FIGS. 1, 2, 3, 4, 5 and 6 respectively.

In terms of intensity of the response to inecalcitol, the classical Hodgkin lymphoma L-428 cell line and the B-acute lymphoblastic leukemia RS4,11 cell line showed the lowest increase in fluorescent labelling with 2- and 2.5-fold, respectively. The two multiple myeloma cell lines (MM.1s and L-363) and the U-937 cell line showed a similar 5-fold maximal increase in fluorescent labelling, while the acute promyelocytic leukemia cell line HL-60 was the most responsive with a maximal increase of 12- to 14-fold increase in basal fluorescent signal.

The invention claimed is:
1. The combination of inecalcitol with an anti-CD38 agent, wherein said anti-CD38 agent is selected from the group consisting of daratumumab, isatuximab, and MOR202.

* * * * *